(12) United States Patent
Martinez

(10) Patent No.: US 9,179,969 B2
(45) Date of Patent: Nov. 10, 2015

(54) SPHINCTEROTOME ORIENTATION

(75) Inventor: Michelle D. Martinez, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 318 days.

(21) Appl. No.: 13/153,056

(22) Filed: Jun. 3, 2011

(65) Prior Publication Data

US 2012/0310265 A1 Dec. 6, 2012

(51) Int. Cl.
- A61B 17/32 (2006.01)
- A61B 18/14 (2006.01)
- A61B 17/00 (2006.01)
- A61B 18/00 (2006.01)

(52) U.S. Cl.
CPC ....... *A61B 18/1492* (2013.01); *A61B 2017/003* (2013.01); *A61B 2018/00535* (2013.01); *A61B 2018/00553* (2013.01); *A61B 2018/00601* (2013.01); *A61B 2018/144* (2013.01)

(58) Field of Classification Search
CPC ................ A61B 18/1492; A61B 2018/00553; A61B 2018/00535; A61B 2018/144; A61B 2014/00601; A61B 2017/003
USPC ........................... 606/113, 144, 170; 600/104
See application file for complete search history.

(56) References Cited

U.S. PATENT DOCUMENTS

| | | | |
|---|---|---|---|
| 2,975,785 A | 3/1961 | Sheldon | |
| 4,369,768 A | 1/1983 | Vukovic | |
| 4,607,622 A | 8/1986 | Fritch et al. | |
| 5,024,617 A * | 6/1991 | Karpiel | 606/47 |
| 5,383,849 A | 1/1995 | Johlin, Jr. | |
| 5,476,497 A | 12/1995 | Mower et al. | |
| 5,609,624 A | 3/1997 | Kalis | |
| 5,810,807 A | 9/1998 | Ganz et al. | |
| 5,984,920 A | 11/1999 | Steinbach | |
| 6,017,339 A | 1/2000 | Sadamasa | |
| 6,017,340 A | 1/2000 | Cassidy et al. | |
| 6,533,782 B2 | 3/2003 | Howell et al. | |
| 6,679,851 B2 * | 1/2004 | Burbank et al. | 600/564 |
| 6,770,066 B1 | 8/2004 | Weaver et al. | |
| 7,056,319 B2 | 6/2006 | Aliperti et al. | |
| 7,780,690 B2 * | 8/2010 | Rehnke | 606/170 |
| 2004/0064128 A1 | 4/2004 | Raijman et al. | |
| 2004/0199121 A1 * | 10/2004 | Wenchell et al. | 604/167.06 |

(Continued)

FOREIGN PATENT DOCUMENTS

JP 1990-279151 A 11/1990
JP 8173374 7/1996

(Continued)

OTHER PUBLICATIONS

International Search Report and Written Opinion dated Sep. 20, 2012 for International Application No. PCT/US2012/040438.

(Continued)

*Primary Examiner* — Thomas McEvoy
*Assistant Examiner* — Julie A Szpira
(74) *Attorney, Agent, or Firm* — Brinks Gilson & Lione

(57) ABSTRACT

A sphincterotome having a pair of ribs that are disposed equidistant from each other about an outer surface of a tubular member of the sphincterotome is disclosed. The pair of ribs is oriented perpendicular to a radial direction in which a cutting edge of a cutting wire disposed at a distal portion of the tubular member extends.

9 Claims, 6 Drawing Sheets

(56) References Cited

U.S. PATENT DOCUMENTS

| | | |
|---|---|---|
| 2005/0101836 A1 | 5/2005 | Onuki et al. |
| 2005/0215996 A1 | 9/2005 | Ouchi |
| 2006/0173241 A1 | 8/2006 | Ouchi et al. |
| 2007/0208221 A1 | 9/2007 | Kennedy, II et al. |
| 2008/0091196 A1 | 4/2008 | Deal |
| 2008/0119738 A1 | 5/2008 | Imahashi et al. |
| 2008/0208001 A1 | 8/2008 | Hadani |
| 2008/0214890 A1 | 9/2008 | Motai et al. |
| 2009/0043259 A1 | 2/2009 | Hardin, Jr. et al. |
| 2009/0093674 A1* | 4/2009 | Adams .......................... 600/104 |
| 2010/0094087 A1 | 4/2010 | Hutchins et al. |
| 2010/0292692 A1* | 11/2010 | Sherwood et al. .............. 606/45 |

FOREIGN PATENT DOCUMENTS

| | | |
|---|---|---|
| JP | 1997-206309 A | 8/1997 |
| JP | 2002-65681 A | 3/2002 |
| WO | WO 2009/020919 | 12/2009 |

OTHER PUBLICATIONS

Japanese Office Action for corresponding Japanese application No. 2014-513741 dated Feb. 10, 2015 including translation.

* cited by examiner

SPHINCTEROTOME ORIENTATION

FIELD OF THE INVENTION

The present invention relates generally to medical devices, and more particularly to sphincterotomes.

BACKGROUND OF THE INVENTION

The biliary tree is an anatomical path that transports bile secreted from the liver to the duodenum of the small intestine. The bile empties into the duodenum at the duodenal papilla. Problems occurring in the biliary tree, such as the formation of bile duct stones or papillary stenosis, are treated using medical devices that are delivered into the biliary tree. In order to access the biliary tree, the medical devices must pass through the sphincter of Oddi, a muscular valve surrounding the papilla that controls the flow of pancreatic juices and bile into the duodenum. The sphincter of Oddi is constrictive in nature, making passage through the sphincter of Oddi difficult. In order to ease passage through the sphincter of Oddi, the sphincter muscle is cut through a medical procedure called a sphincterotomy.

A sphincterotomy is performed using a medical device called a sphincterotome. An example of a sphincterotome is found in United States Patent Application Publication No. 2009/0043259, and is incorporated herein by reference. A sphincterotome comprises an elongate tubular member with a plurality of lumens extending therethrough. Typically, a cutting wire that is used to cut the sphincter muscle is disposed within one of the lumens. In addition, a wire guide is disposed within another lumen, and a third lumen may be used to inject contrast at the cutting site.

The cutting wire is disposed within one of the lumens except at a distal portion of the tubular member. At the distal portion, the cutting wire is exposed outside of the lumen and along the tubular member. The portion of the cutting wire outside of the lumen, called the cutting edge, is used to cut the sphincter muscle.

A sphincterotomy generally involves a two-part process: cannulation of the biliary tree and cutting the sphincter muscle by sending an electric current through the cutting wire (i.e, electrocautery). Cannulation of the biliary tree involves inserting the distal portion of the tubular member into the papilla and using the distal portion and the cutting edge to lift the upper portion (i.e., the roof) of the papilla. In particular, after the distal portion is inserted into the papilla, the roof of the papilla is lifted by proximally pulling the cutting wire taut. Proximally pulling the cutting wire taut causes the distal portion of the tubular member to bow and form an arc. The cutting edge, being taut, forms a secant of the arc and lifts the roof of the papilla.

Lifting the roof of the papilla, as opposed to moving other portions of the papilla, is optimal for cannulating the biliary tree because the cutting edge and the distal portion can enter the biliary tree without injuring the duodenal wall or pancreatic duct. Accordingly, the distal portion of the tubular member is inserted into the papilla with the cutting edge radially extending upward because ideally, the distal portion curls in the direction in which the cutting edge radially extends. However, in practice, the distal portion may not curl in the direction that the cutting edge faces. The size, shape, and position of the lumens within the tubular member affect the center of moment of the tubular member and ultimately the curling direction of the distal portion. As a result, even if the distal portion is inserted into the papilla with the cutting edge facing upward, the distal portion may not curl upward to lift the roof of the papilla when the cutting wire is proximally pulled.

BRIEF SUMMARY OF THE INVENTION

The present disclosure is directed to a sphincterotome used to perform a sphincterotomy at a cutting site within a patient. The sphincterotome includes an elongate tubular member having a pair of ribs circumferentially disposed equidistant from each other about an outer surface of the tubular member. The tubular member has at least two lumens longitudinally extending therethrough. A cutting wire is at least partially disposed within one of the lumens. The cutting wire has a cutting edge that is disposed outside of the tubular member. The cutting edge longitudinally extends along a distal portion of the tubular member and radially extends in an outward direction from the outer surface of the tubular member. The pair of ribs is oriented perpendicular to the outward direction in which the cutting edge radially extends.

The present disclosure is further directed to a sphincterotome having a cross-sectional profile that includes a thickened portion that extends across an otherwise circular cross section. The thickened portion has a maximum length that is greater than the diameter of the otherwise circular cross section. The thickened portion may have an obround shape. The sphincterotome includes at least two lumens extending therethrough, where one of the lumens contains a cutting wire. The cutting wire has a cutting edge that is disposed outside of tubular member. The cutting edge longitudinally extends along a distal portion of the tubular member and radially extends in an outward direction from an outer surface of the tubular member. The thickened portion extends perpendicular to the outward direction in which the cutting edge radially extends. In one embodiment, the thickened portion longitudinally extends from a proximal portion of the tubular member to the distal portion of the tubular member. In an alternative embodiment, the thickened portion longitudinally extends only at the distal portion of the tubular member. In the alternative embodiment, the proximal portion of the tubular member has a circular cross-sectional profile.

The present disclosure is further directed to a sphincterotome used to perform a sphincterotomy at a cutting site within a patient that includes an elongate tubular body and a tubular sleeve disposed over an outer surface of the tubular body. A pair of ribs is circumferentially disposed equidistant from each other on the sleeve. A cutting edge is disposed outside the tubular body, longitudinally extending along a distal portion of the tubular body and radially extending in an outward direction. The pair of ribs is oriented perpendicular to the outward direction in which the cutting edge radially extends.

DETAILED DESCRIPTION OF THE INVENTION

Figure 1:
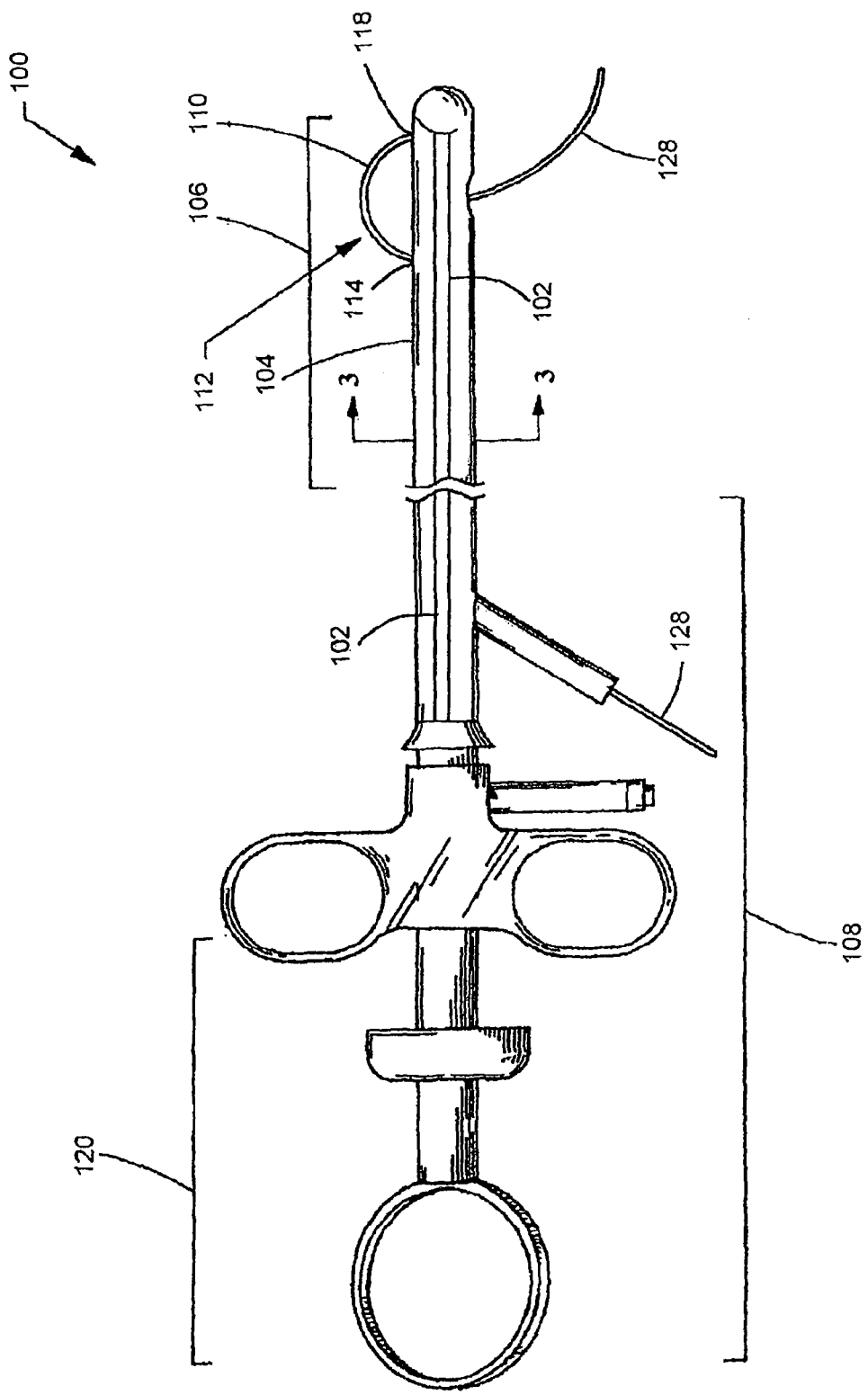
FIG. 1 is a side view of a sphincterotome in a relaxed state showing one of a pair of ribs disposed on an outer surface of the sphincterotome.

FIG. 1 shows a side view of a sphincterotome 100 having a pair of ribs 102 disposed about an outer surface of a tubular member 104. The tubular member 104 of the sphincterotome 100 has a distal portion 106 and a proximal portion 108. In one embodiment, as shown in FIG. 1, the pair of ribs 102 longitudinally extends from the proximal portion 108 to the distal portion 106 of the tubular member 104. Alternatively, the pair of ribs 102 is disposed about the outer surface only at the distal portion 106. For example, the pair of ribs 102 may be three to six centimeters long and disposed at the distal portion 106 of the tubular member 104.

FIG. 1 also shows a cutting edge 110 of a cutting wire 112 at the distal portion 106 of the tubular member 104. The cutting edge 110 is located outside of the tubular member 104. The cutting edge 110 radially extends in an outward direction from the outer surface of the tubular member 104. In FIG. 1, the sphincterotome 100 is oriented with the outward direction being upward. The cutting edge 110 projects from a wall of the tubular member 104 through a proximal opening 114 located at the distal portion 106 of the tubular member 104. The cutting edge 110 is connected to a conductor component 116 (not shown in FIG. 1) of the cutting wire 112. The conductor component 116 is disposed within a cutting wire lumen (not shown in FIG. 1) of the tubular member 104. The cutting edge 110 is oriented generally longitudinal with respect to the tubular member 104 and extends along the distal portion 106 of the tubular member 104. The cutting edge 110 re-enters the wall of the tubular member 104 through a distal opening 118 located at the distal portion 106 of the tubular member 104 and is secured inside the tubular member 104 near the distal opening 118.

Figure 2:
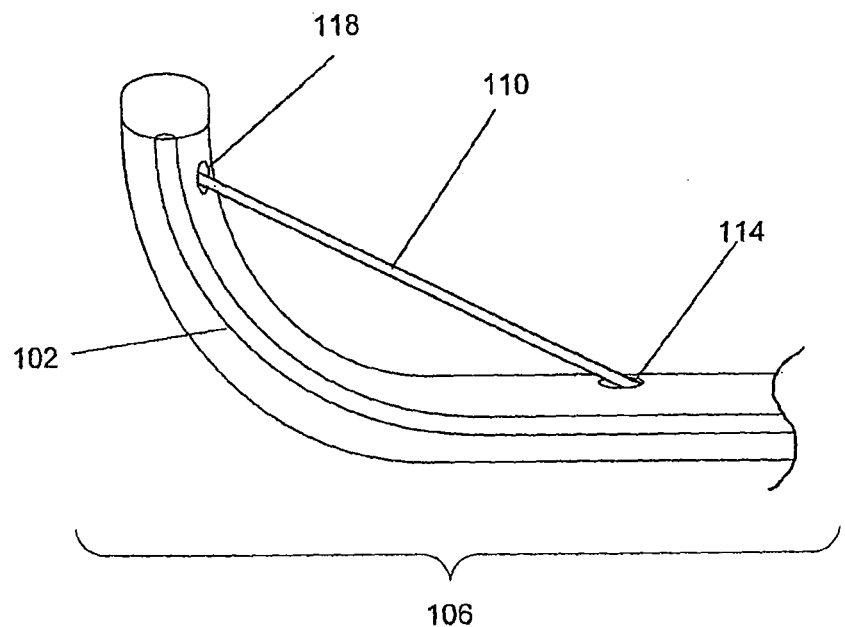
FIG. 2 is a side view of a distal portion of the sphincterotome of FIG. 1 showing the distal portion curled and the cutting edge in a cutting state.

In FIG. 1, the cutting edge 110 is shown in a relaxed state. Actuation of a control handle assembly 120 moves the cutting edge 110 from the relaxed state to a cutting state by proximally pulling the cutting wire 112 taut. Pulling the cutting wire 112 taut causes the distal portion 106 of the tubular member 104 to bow or curl and form an arc. FIG. 2 shows the distal portion 106 of the tubular member 104 in a curled state with the cutting wire 112 taut and the cutting edge 110 in a cutting state. Geometrically, when the distal portion 106 is in a curled state, the distal portion 106 forms an arc and the cutting edge 110 forms a secant of the arc. When viewing the sphincterotome 100 along the longitudinal axis of the sphincterotome, the radial direction in which the distal portion curls is referred to as a curling direction.

Figure 3:
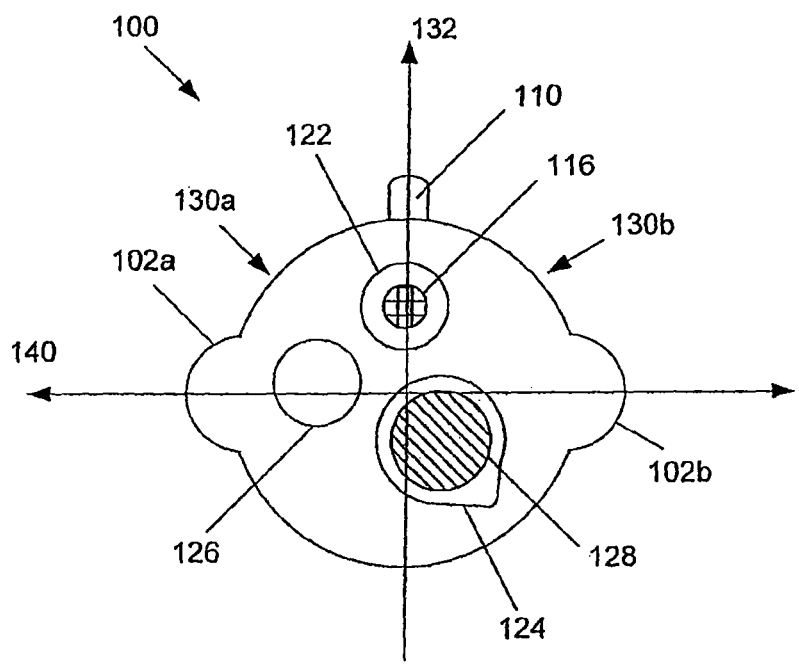
FIG. 3 is a cross-sectional view of FIG. 1 taken along line 3-3.

FIG. 3 is a cross-sectional view of one embodiment of the sphincterotome 100 taken along line 3-3 in FIG. 1. The tubular member includes multiple lumens. In the embodiment shown in FIG. 3, the sphincterotome 100 has three lumens—a cutting wire lumen 122, a wire guide lumen 124, and a contrast lumen 126. In an alternative embodiment, the tubular member 104 has only a cutting wire lumen 122 and a wire guide lumen 124. The cutting wire lumen 122 contains the conductor component 116 of the cutting wire 112. The wire guide lumen 124 contains a wire guide 128. The contrast lumen 126 is used to inject a contrast medium at the cutting site. In the embodiment of the sphincterotome shown in FIG. 3, the cutting wire lumen 122 and the contrast lumen 126 have circular cross-sectional shapes and the wire guide lumen 124 has a teardrop shape. In addition, the wire guide lumen 124 is larger than the cutting wire lumen 122 and the contrast lumen 126.

FIG. 3 also shows the cutting edge 110 exposed outside of the tubular member 104. In FIG. 3, the distal portion 106 is oriented so that the cutting edge 110 is facing in an upward direction. When the cutting edge 110 is facing in an upward direction, the cutting wire lumen 122 is positioned generally above the wire guide lumen 124 and the contrast lumen 126.

Figure 4:
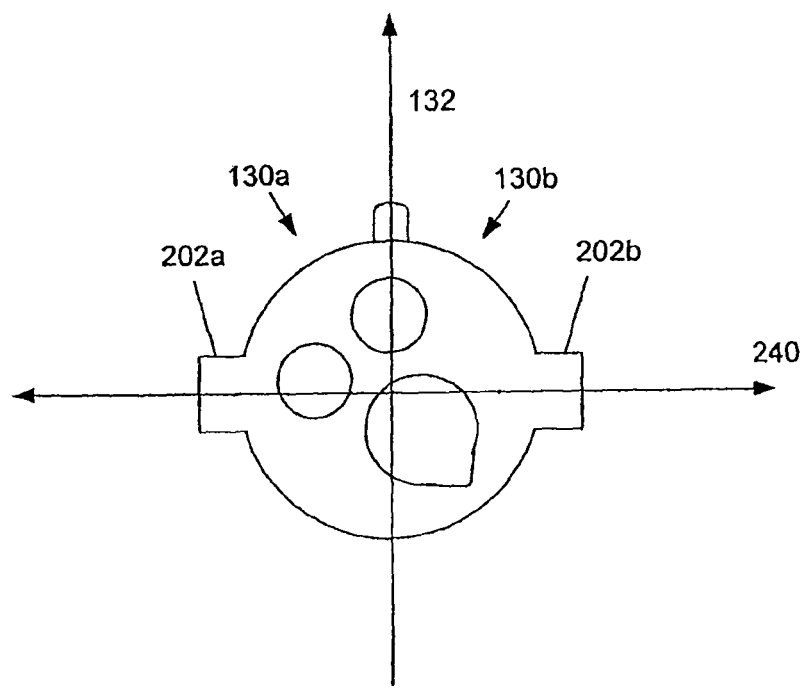
FIG. 4 is a cross-sectional view of an alternative embodiment of the sphincterotome.
Figure 5:
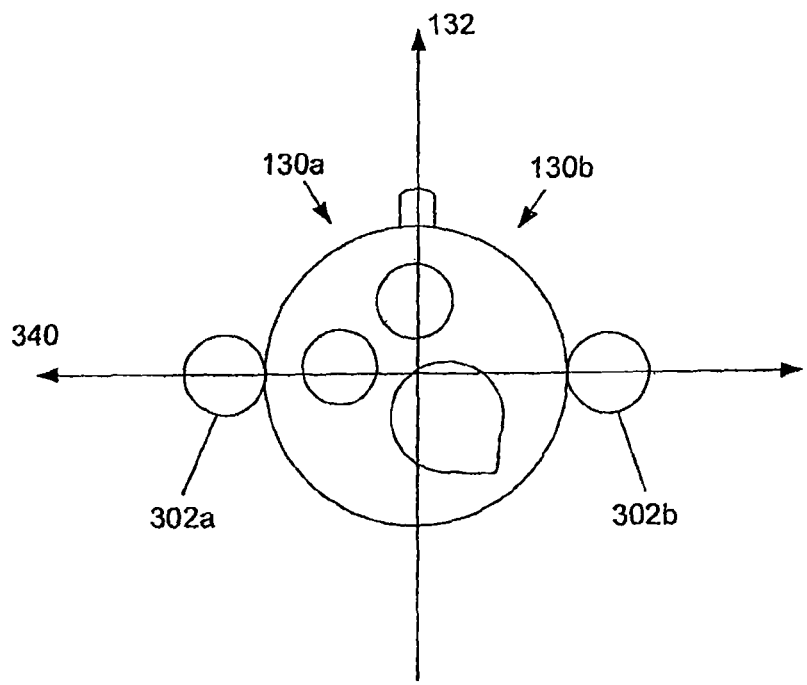
FIG. 5 is a cross-sectional view of a second alternative embodiment of the sphincterotome.
Figure 6:
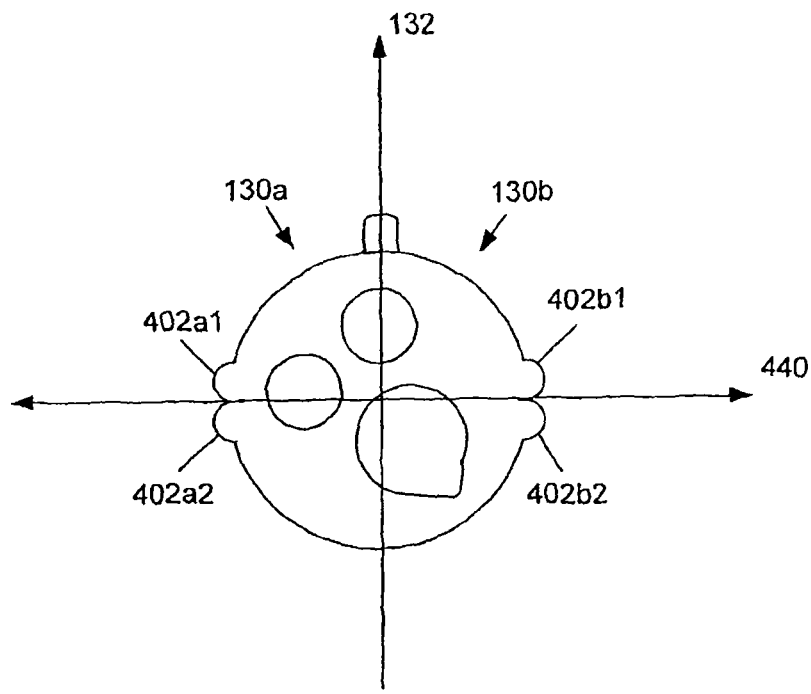
FIG. 6 is a cross-sectional view of a third alternative embodiment of the sphincterotome.
Figure 7:
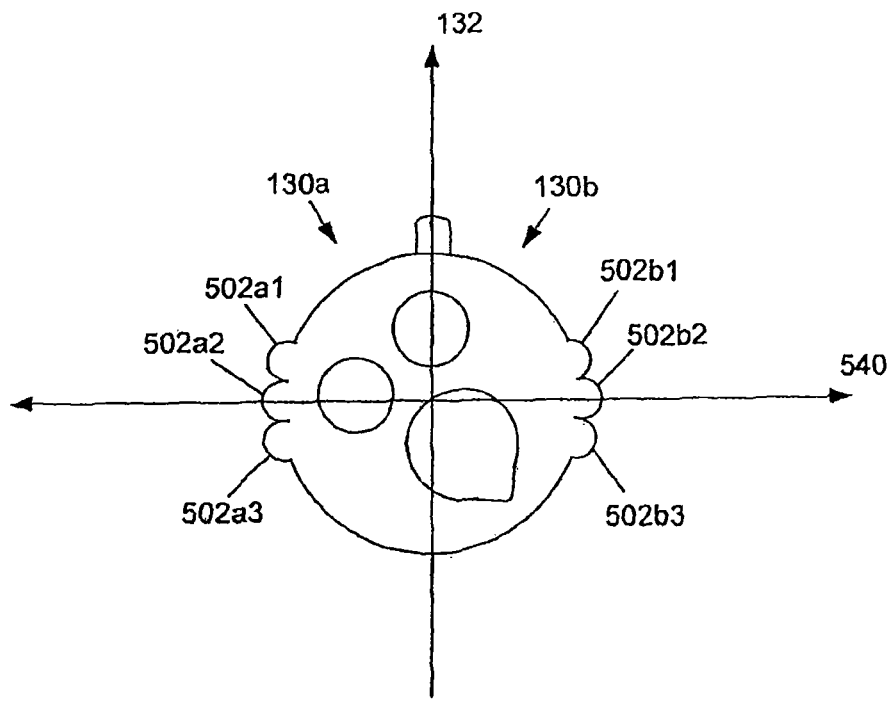
FIG. 7 is a cross-sectional view of a fourth alternative embodiment of the sphincterotome.

Additionally, FIG. 3 shows the pair of ribs 102a, 102b circumferentially disposed about an outer surface of the tubular member 104. The ribs 102a, 102b have a semi-circular cross-sectional profile and protrude from an otherwise circular profile of the tubular member. FIGS. 4-7 show alternative embodiments of the ribs. FIG. 4 shows a pair of ribs 202 having rectangular cross-sectional profiles and protruding from an otherwise circular profile of the tubular member 204. FIG. 5 shows a pair of ribs 302 having circular cross-sectional profiles. FIGS. 6 and 7 show alternative embodiments where each rib is replaced with a plurality of ribs. FIG. 6 shows an alternative embodiment where each rib 402a, 402b comprises two ribs 402a1, 402a2, 402b1, 402b2. In FIG. 6, the ribs have semi-circular cross-sectional profiles protruding from an otherwise circular cross-sectional profile of the tubular member 404. FIG. 7 shows an alternative embodiment where each rib 502a, 502b comprises three ribs 502a1, 502a2, 502a3, 502b1, 502b2, 502b3. In FIG. 7, the ribs 502a1-a3, 502b1-b3 have semi-circular cross-sectional profiles protruding from an otherwise circular cross-sectional profile of the tubular member.

For each of the pair of ribs shown in FIGS. 3-7, the two ribs have the same cross-sectional shapes. However any combination of the shapes shown in FIGS. 3-7 may be used. Also, other cross-sectional shapes may be used in addition to semi-circular, circular, and rectangular shapes. For example, triangular, pentagonal, hexagonal, or octagonal cross-sectional shapes may be used. In addition, more than three ribs may be used to replace a single rib. In general, ribs denote those portions of the sphincterotome additional to the circular cross-sectional profile of the tubular member that are circumferentially disposed about the outer surface of the tubular member and that longitudinally extend along at least a portion of the tubular member.

As shown in FIGS. 3-7, the ribs 102, 202, 302, 402, 502 are disposed equidistant from each other about the outer surface of the tubular member 104. Because the ribs are disposed equidistant from each other, the distance in a clockwise direction about the surface of the tubular member from a center point of one of the ribs to a center point of the other rib is the same as the distance in a counter-clockwise direction about the surface of the tubular member from the center point of one the ribs to the center point of the other rib. Where the each rib is replaced by a plurality of ribs, such as in FIGS. 6 and FIGS. 7, the center point for each of the plurality of ribs is generally the middle of the ribbed region about the outer surface. In FIG. 6, the center point of the plurality or ribs 402a1, 402a2 is the middle point on the outer surface between rib 402a1 and rib 402a2. Likewise, the center point of the plurality of ribs 402b1, 402b2 is the middle point on the outer surface between rib 402b1 and rib 402b2. In FIG. 7, the center point of the plurality of ribs 502a1-a3 is the center of rib 502a2. Likewise, the center point of the plurality of ribs 502b1-b3 is the center of rib 502b2.

Shown in FIGS. 3-7, the cross-sectional profile of the sphincterotome is separated into a first side 130a and a second side 130b. The two sides 130a, 130b are determined by the outward direction in which the cutting edge 110 radially extends. Generally, one of the pair of ribs is circumferentially disposed about the outer surface of the tubular member 104 on one side, and the other of the pair of ribs is circumferentially disposed about the outer surface of the tubular member 104 on the other side. For example, in FIG. 3, rib 102a is circumferentially disposed about the outer surface of the tubular member 104 on the first side 130a, and rib 102b is circumferentially disposed about the tubular member on the second side 130b. Where each rib is replaced with a plurality of ribs, such as in FIGS. 6 and 7, one of the plurality of ribs is on one side, and the other of the plurality of ribs is on the other side. For example, in FIG. 6, rib 402a1 and rib 402a2 are both on the first side, and rib 402b1 and rib 402b2 are both on the second side.

The pair of ribs has an orientation circumferentially about the outer surface of the tubular member 104. The orientation is defined by a line intersecting the center points of the pair of ribs. For example, in FIG. 3, the orientation of the pair of ribs 102a, 102b is defined by double-sided arrow 140 intersecting the center point of rib 102a and the center point of rib 102b. In FIG. 4, the orientation of the pair of ribs 202a, 202b is defined by double-sided arrow 240 intersecting the center point of rib 202a and the center point of rib 202b. In FIG. 5, the orientation of the pair of ribs 302a, 302b is defined by double-sided arrow 340 intersecting the center point of rib 302a and the center point of rib 302b. Where each rib is replaced with a plurality of ribs, such as in FIGS. 6 and 7, the orientation of the ribs is defined by a double-sided arrow intersecting the center point of each of the plurality of ribs. In FIG. 6, the orientation of the pair of two ribs 402a1, 402a2 and 402b1, 402b2 is defined by double-sided arrow 440 intersecting the center point of ribs 402a1, 402a2 and the center point of ribs 402b1, 402b2. In FIG. 7, the orientation of the pair of three ribs 502a1-a3, 502b1-b3 is defined by double-sided arrow 540 intersecting the center point of rib 502a2 and the center point of rib 502b2.

The orientation of the pair or ribs, as defined by double-sided arrow 140, 240, 340, 440, 540 in FIGS. 3-7, is perpendicular to the outward direction in which the cutting edge 110 radially extends. Shown in FIGS. 3-7, the outward direction is designated by arrow 132. Generally, the pair of ribs thickens a portion of an otherwise circular cross-sectional profile of the tubular member 104. A maximum length of the thickened portion has a length that is greater than the diameter of the otherwise circular cross-sectional profile. As shown in FIG. 3, where the ribs 102a, 102b have a semi-circular cross-sectional profile, the thickened portion has an obround shape. The thickened portion radially extends perpendicular to the outward direction in which the cutting edge 110 radially extends. The thickened portion increases the volume of the cross section of the tubular member 104 in radial directions perpendicular to the radial direction in which the cutting edge 110 extends. Increasing the volume stiffens the tubular member 104 in the radial directions perpendicular to the outward radial direction of the cutting edge 110, making movement, such as bending or curling, of the sphincterotome 100 in the radial directions perpendicular to the outward radial direction of the cutting edge 110 more difficult. As a result, the tendency of the sphincterotome to curl in the outward radial direction of the cutting edge 110 is enhanced.

FIGS. 3-7 show the sphincterotome oriented so that the outward direction in which the cutting edge 110 radially extends is upward. In addition, the orientation of the pair of ribs 102, 202, 302, 402, 502, being perpendicular to the upward direction is a horizontal direction. Because the pair of ribs is oriented horizontally, curling or bending of the distal portion 106 of the tubular member 104 in the horizontal direction is more difficult. As a result, the tendency of the sphincterotome 100 to bend or curl in the outward direction in which the cutting edge 110 radially extends (e.g., an upward direction) is enhanced.

Figure 8:
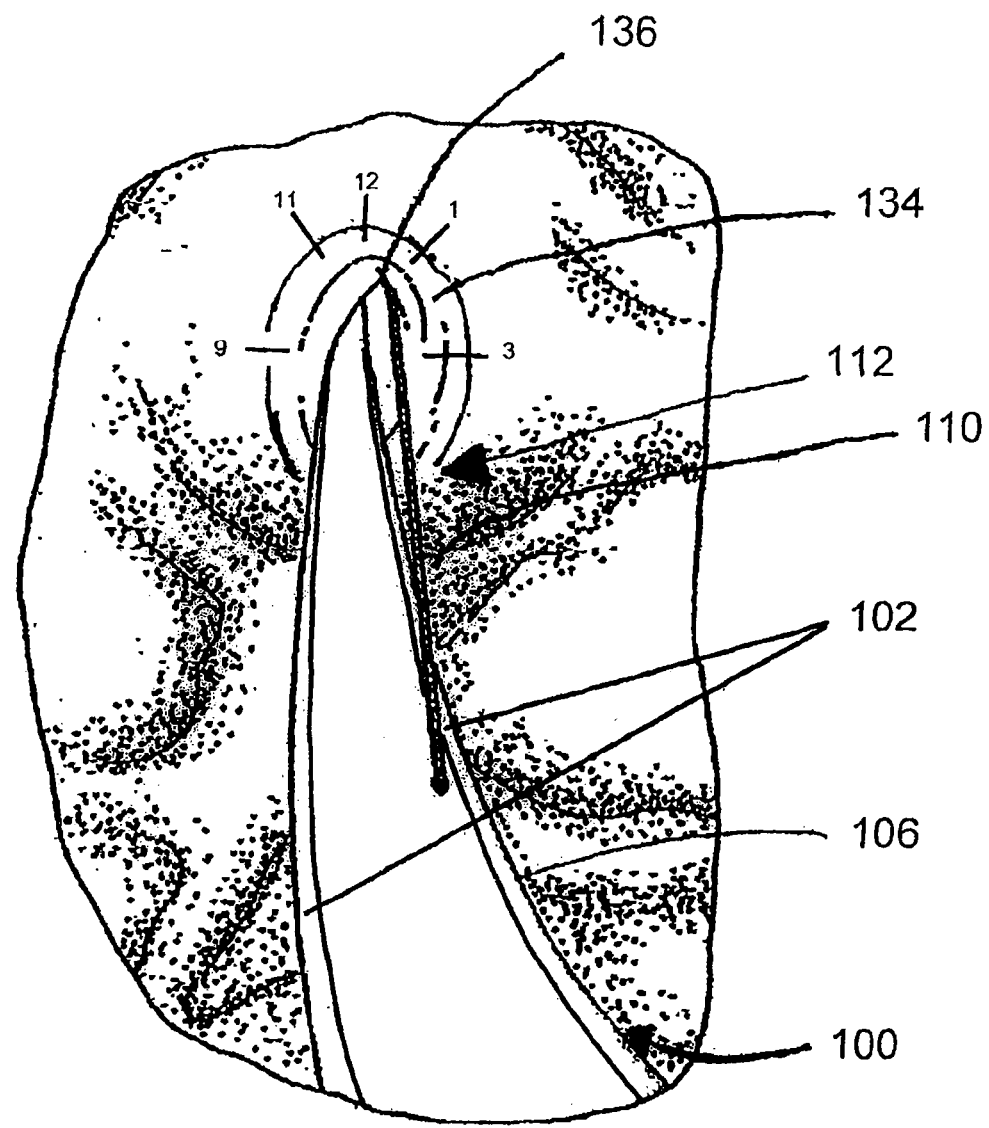
FIG. 8 is a perspective view of a sphincterotome accessing a patient's papilla.

FIG. 8 shows the distal portion 106 sphincterotome 100 accessing a patient's papilla 134. In FIG. 8, designations 12, 1, 3, 9, 10, and 11 correspond to the positions of 12 o'clock, 1 o'clock, 3 o'clock, 9 o'clock, and 11 o'clock respectively around the papilla 134. An upper portion or roof 136 of the papilla 134 generally extends from the 11 o'clock position to the 1 o'clock position. In FIG. 8, the sphincterotome 100 is in the 12 o'clock position with the cutting edge 110 facing upward and aligned to the 12 o'clock position. Positioning the sphincterotome 100 so that the cutting edge 110 is aligned to the 12 o'clock position and facing upward is the optimal position for cannulating the biliary tree because in the 12 o'clock position, the cutting edge 110 can lift the roof 136 of the papilla 134 without injuring the duodenal wall or the pancreatic duct. Shown in FIG. 8, by positioning the sphincterotome in the 12 o'clock position, the ribs 102a, 102b are at the 9 o'clock and 3 o'clock positions, respectively. The ribs 102a, 102b at the 9 o'clock and 3 o'clock positions increase the tendency for the distal portion 106 of the tubular member 104 to curl in the upward direction (i.e., toward 12 o'clock) when the cutting wire 112 is proximally pulled.

Figure 9:
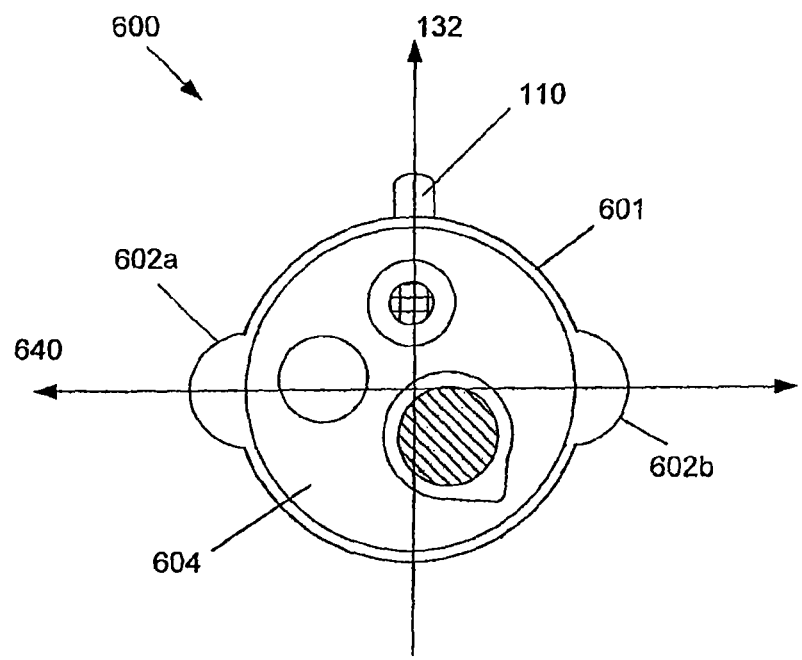
FIG. 9 is a cross-sectional view of a fifth alternative embodiment of the sphincterotome, showing a sleeve having ribs disposed over a tubular member of the sphincterotome.

The sphincterotome may be manufactured by co-extruding the pair of ribs and the tubular member. Alternatively, the pair of ribs may be produced separately and attached to the tubular member. For example, the ribs may be produced as part of a tubular sleeve and the sleeve is disposed over the tubular member. FIG. 9 shows a cross-sectional view of a sphincterotome 600 having a tubular sleeve 601 disposed over a tubular body 604 of the sphincterotome 600. As shown in FIG. 9, the sleeve 601 has ribs 602a, 602b circumferentially disposed equidistant from each other on the sleeve. The sleeve 601 is positioned over the tubular member 604 so that the ribs 602a, 602b are oriented perpendicular to an outward direction in which the cutting wire 110 extends.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

I claim:

1. A sphincterotome used to perform a sphincterotomy at a cutting site within a patient, the sphincterotome comprising:
    an elongate tubular member having a proximal portion and a distal portion, the proximal portion extending and connected to a control handle assembly configured to curl the distal portion in a curling direction by pulling taut a cutting wire;
    at least two lumens longitudinally extending through the elongate tubular member, one of the at least two lumens having the cutting wire at least partially disposed therein; and a single pair of ribs circumferentially disposed equidistant from each other about an outer surface of the tubular member and longitudinally extending from the proximal portion to the distal portion, wherein the single pair of ribs is circumferentially oriented about the outer surface perpendicular to the curling direction and adapted to curl with the elongate tubular member in the curling direction at the distal portion when the control handle assembly pulls taut the cutting wire, wherein the single pair of ribs in combination with the outer surface forms a cross-sectional profile of the elongate tubular member that comprises a thickened portion extending across an otherwise circular cross-section, wherein the thickened portion has a maximum length that is greater than a diameter of the otherwise circular cross-section, and wherein the cross-sectional profile is uniform over a longitudinal length in which the single pair of ribs longitudinally extends from the proximal portion to the distal portion;

wherein the cutting wire comprises a cutting edge disposed outside of the tubular member, the cutting edge longitudinally extending along the distal portion of the tubular member and radially extending outwardly in the curling direction from the outer surface of the tubular member.

2. The sphincterotome of claim 1, wherein the at least two lumens comprises a first lumen, a second lumen, and a third lumen, the first lumen having the cutting wire at least partially disposed therein, the second lumen having a wire guide disposed therein, and the third lumen used to inject a contrast agent at the cutting site.

3. The sphincterotome of claim 1, wherein each rib of the single pair of ribs has a semi-circular cross-sectional profile.

4. The sphincterotome of claim 1, wherein the single pair of ribs is co-extruded with the tubular member.

5. The sphincterotome of claim 1, wherein each rib of the single pair of ribs comprises two smaller ribs next to each other about the outer surface.

6. The sphincterotome of claim 1, wherein the single pair of ribs is integral with the elongate tubular member.

7. The sphincterotome of claim 1, wherein the single pair of ribs is solid over the longitudinal length in which the pair of ribs longitudinally extends.

8. A sphincterotome used to perform a sphincterotomy at a cutting site within a patient, the sphincterotome comprising;

an elongate tubular member extending from a proximal portion to a distal portion, the proximal portion extending and connected to a control handle assembly configured to curl the distal portion in a curling direction by pulling taut a cutting wire, wherein a cross-sectional profile of the tubular member longitudinally extending from the proximal portion to the distal portion comprises a thickened portion extending across an otherwise circular cross-section, the thickened portion having a maximum length that is greater than a diameter of the otherwise circular cross section, wherein the thickened portion of the cross-sectional profile radially extends perpendicular to the curling direction and is adapted to curl in the curling direction at the distal portion when the control handle assembly pulls taut the cutting wire, and wherein the cross-sectional profile is uniform over a longitudinal length from the proximal portion to the distal portion in which the cross-sectional profile longitudinally extends;

at least two lumens longitudinally extending through the elongate tubular member, one of the at least two lumens having the cutting wire at least partially disposed therein; and wherein the cutting wire comprises a cutting edge disposed outside of the tubular member, the cutting edge longitudinally extending along a distal portion of the tubular member and radially extending outwardly in the curling direction from an outer surface of the tubular member.

9. The sphincterotome of claim 8, wherein the thickened portion has an obround shape.

* * * * *